(12) United States Patent
Vaillancourt

(10) Patent No.: US 6,273,869 B1
(45) Date of Patent: Aug. 14, 2001

(54) VALVE CONNECTOR

(76) Inventor: Vincent L. Vaillancourt, 14 Bunyan Dr., Livingston, NJ (US) 07039

( * ) Notice: Subject to any disclaimer, the term of this patent is extended or adjusted under 35 U.S.C. 154(b) by 0 days.

(21) Appl. No.: 08/956,902

(22) Filed: Oct. 23, 1997

Related U.S. Application Data

(63) Continuation-in-part of application No. 08/663,489, filed on Jun. 13, 1996, now abandoned.

(51) Int. Cl.⁷ ........................................ A61M 5/00
(52) U.S. Cl. ................. 604/86; 604/88; 604/905
(58) Field of Search ............... 604/86, 88, 523, 604/274, 905

(56) References Cited

U.S. PATENT DOCUMENTS 5,575,769 * 11/1996 Vaillancourt ........................ 604/86

* cited by examiner

Primary Examiner—John D. Yasko
(74) Attorney, Agent, or Firm—Francis C Hand, Esq.; Carella, Byrne, Bain, Gilfillan, Cecchi, Stewart & Olstein

(57) ABSTRACT

The hollow cannula is made with a smooth tip to avoid sharp corners on the inside diameter or outside diameter in order to avoid scraping or scoring of a slit or pre-pre-pierced septum during passage through the septum. The cannula may be employed in various types of embodiments including swabable valve connectors.

34 Claims, 6 Drawing Sheets

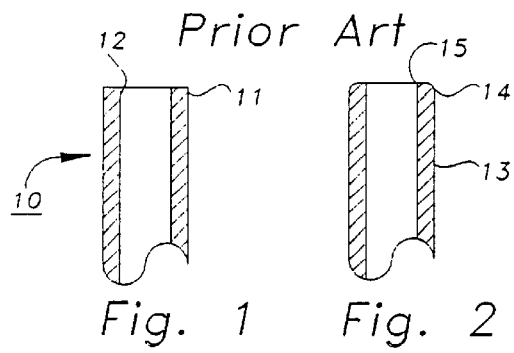
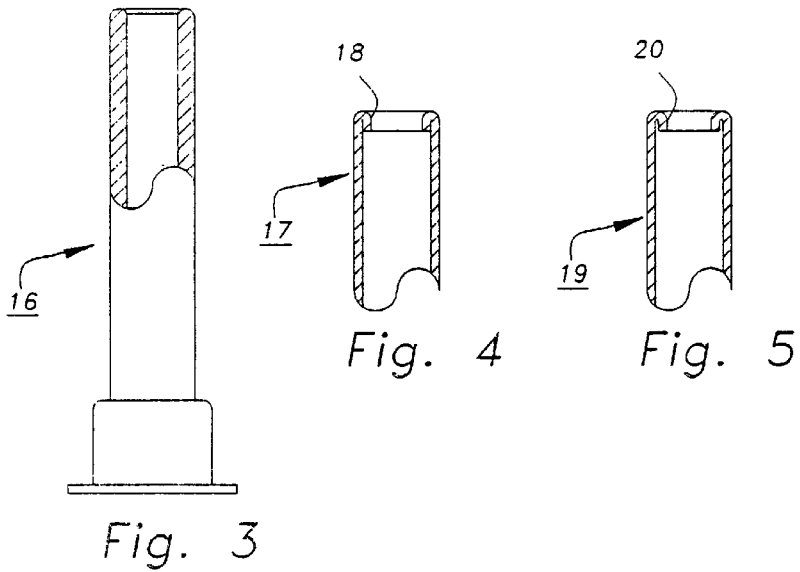
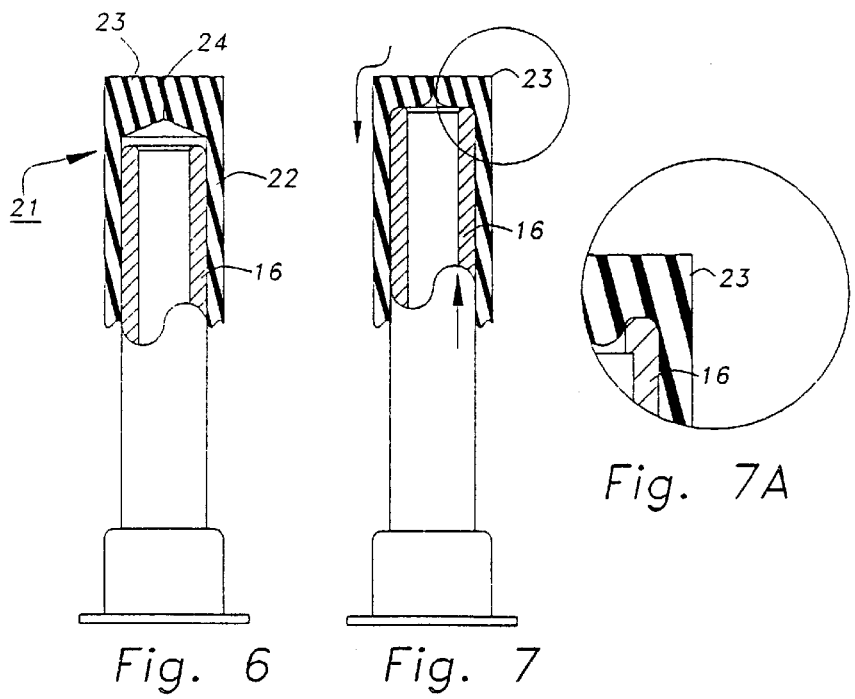
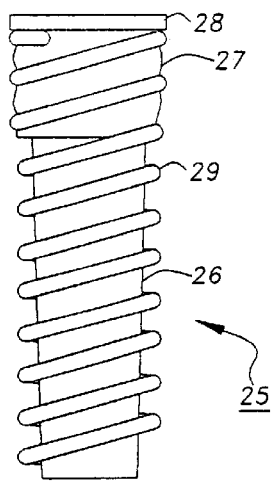

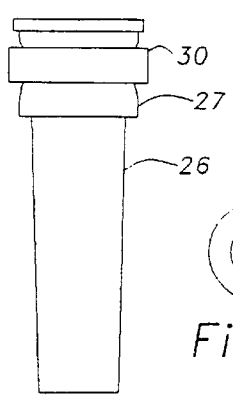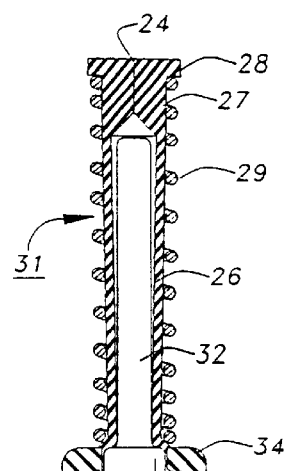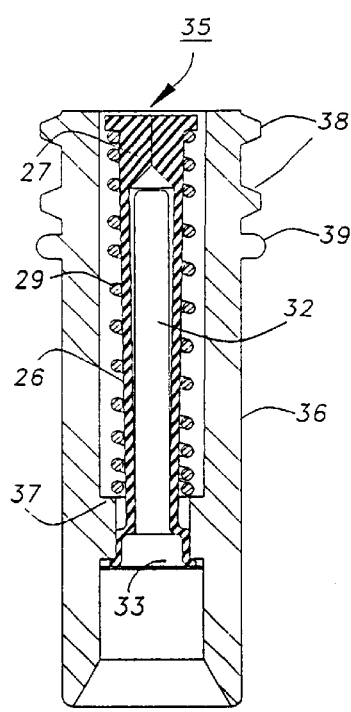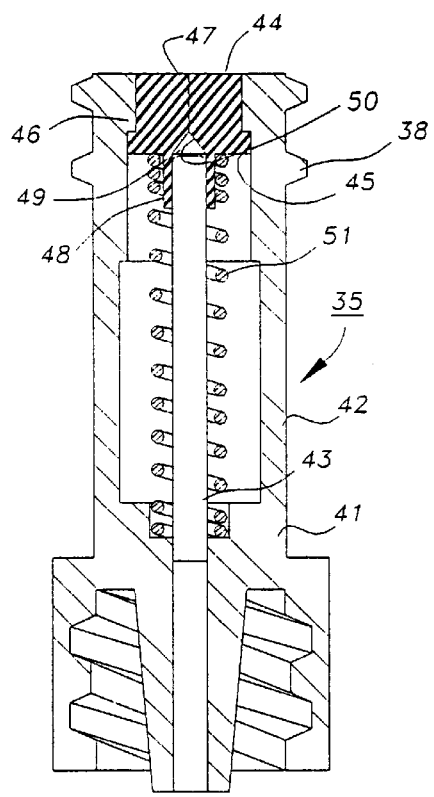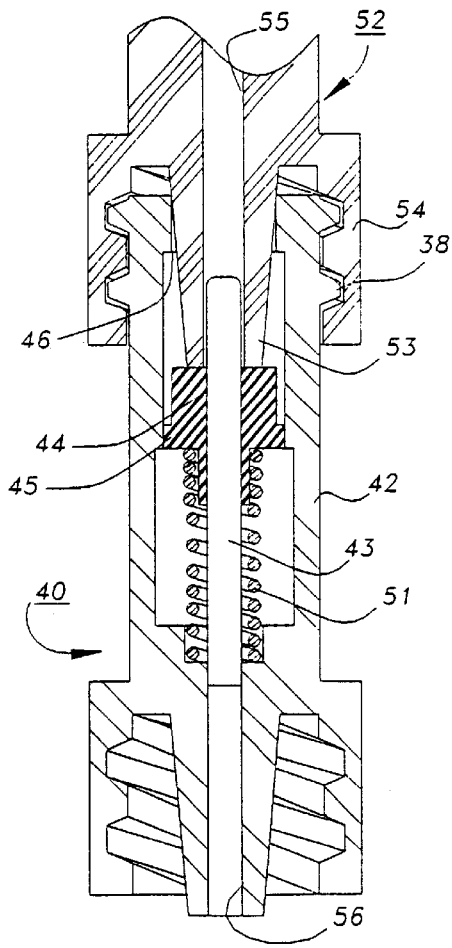
Fig. 9
Fig. 9A
Fig. 10
Fig. 10A
Fig. 11
Fig. 11A

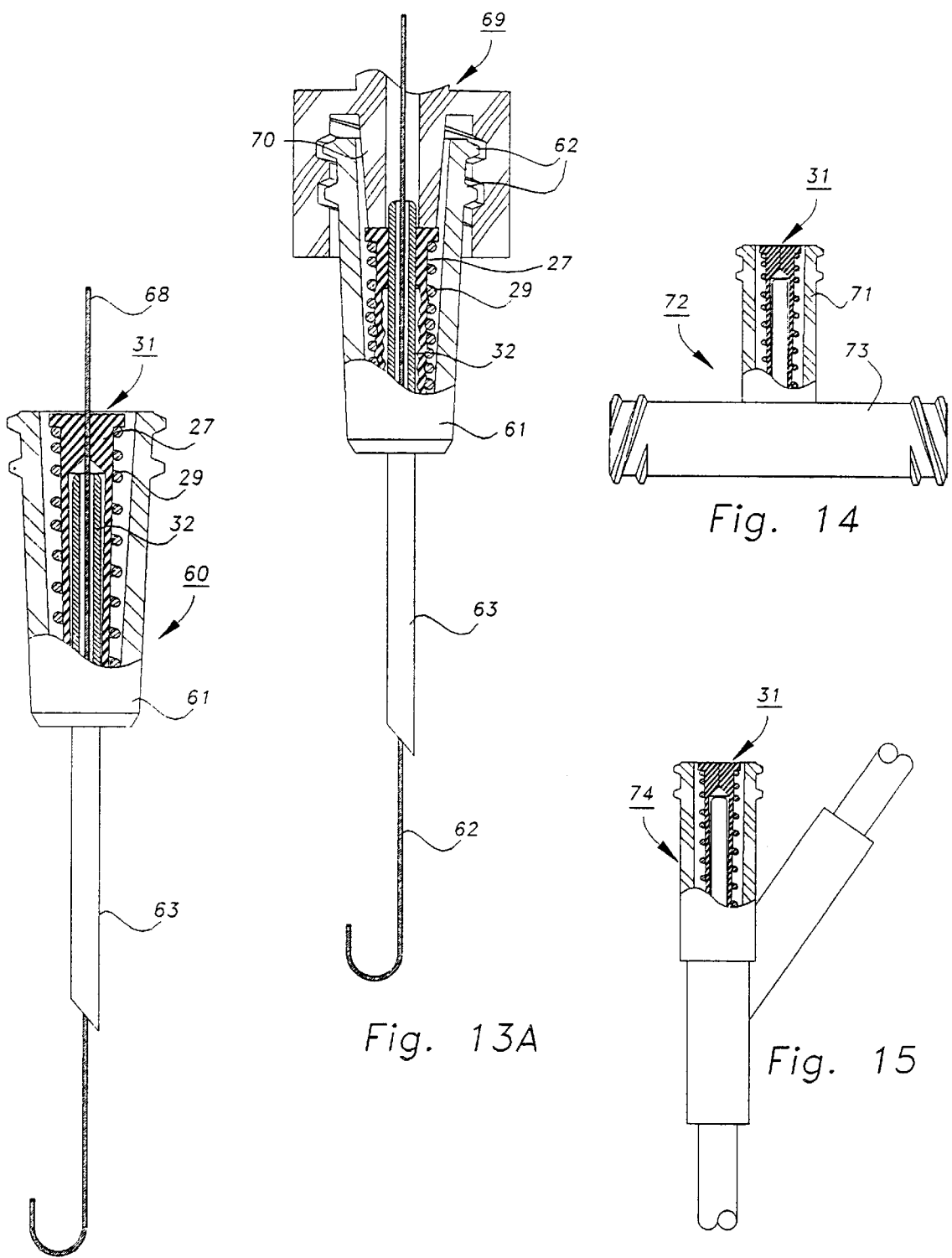

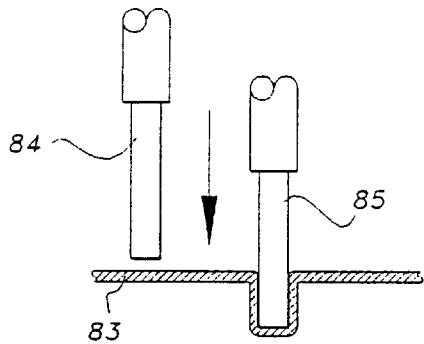
Fig. 18
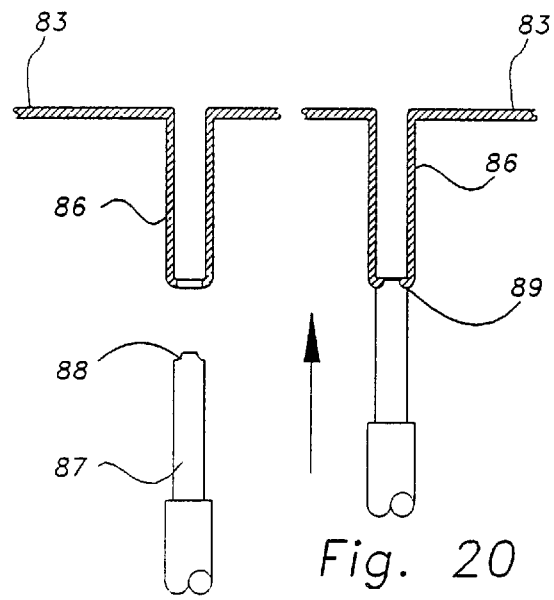
Fig. 20
Fig. 19
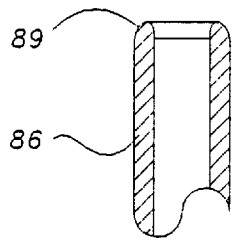
Fig. 21

VALVE CONNECTOR

This is a continuation-in-part of U.S. Ser. No. 08/663,489 filed Jun. 13, 1996, now abandoned the contents of which are incorporated by reference herein.

This invention relates to a valve connector. More particularly, this invention relates to a valve connector which may be swabable. Still more particularly, this invention relates to a valve connector having a straight through lumen path for fluids.

As is known, various types of structures have been employed in the medical field for conveying fluids, such as blood, into and out of a patient. For example, there are a number of swabable valve connectors which have been marketed as needleless types and which use multiple flow paths for the fluid which passes to or from a patient. That is to say, the fluid is separated into two or more paths to flow in annular spaces during the time the fluid traverses through the connector. In those cases where the flow path has been unitary, such as through one tube or one lumen, the connectors have suffered from having very limited coupling life. By this is meant that either the connector begins to leak after only a few uses or, in cases where a needle passes through a membrane, coring of the membrane occurs which generally leads to leakage.

Various types of needleless connectors and access devices have been described in U.S. Pat. Nos. 5,549,577; 5,514,116; 5,509,912; 5,487,728; 5,474,536; 5,441,487; 5,380,306 and 5,360,413. International Patent Application WO96/13301 also describes a similar type of infusion device.

Typically, these publications describe structures which employ either a needle having a sharp end for piercing through a membrane or a blunt cannula for passage through a slit membrane. In the case of a needle, a "coring" effect takes place each time the needle pierces the membrane so that after only a few piercings, a leakage path is formed. In addition, during piercing of the membrane, the sharp end of the needle tends to sliver the membrane so that there is a risk that debris may pass into the lumen of the needle and thus into the patient.

In the case of blunt cannulae, it has been found that although the number of penetrations before leakage occurs is greater than with a needle, there is a significant generation of debris which leads to a very limited product life. In this respect, it has been found that when a blunt cannula abuts the membrane, the membrane penetrates slightly into the opening of the cannula so that the sharp corners which typically exist on the inside diameter of the cannula abrade the membrane so that debris is formed which passes into the lumen of the cannula. As the blunt cannula continues to penetrate through the membrane, the sharp internal corner of the cannula scrapes along the face of the membrane creating a slivering action.

Accordingly, it is an object of this invention to be able to repeatedly open and close a connector without leakage and coring of a membrane of septum.

It is another object of the invention to be able to introduce a guide wire, needle or cannula within a seal area of a valve for extended periods of time without loosing valve sealing properties.

It is another object of the invention to be able to retrofit existing connector housings with a valve structure.

It is another object of the invention to reduce the risk of forming debris when passing a smooth cannula through a slit septum.

Briefly, the invention is directed to a connector comprised, in part, of a pre-pierced septum (or membrane) of elastomeric material having a preformed passage in the form of a slit or preformed hole therein and a hollow cannula for penetrating the septum through the preformed passage wherein the cannula has an open distal end for passage of fluid therethrough and wherein the end has a peripheral wall terminating in a smooth surface for penetrating into the septum without generating debris from the septum.

Typically, the peripheral wall of the distal end of the cannula is folded inwardly to define a rounded surface, for example the rounded end of the cannula can be formed employing eyelet technology.

It has been found that when a smooth cannula is used as the interfacing object between the pre-pierced septum and the cannula (fluid conveying lumen), the risk of generating debris is severely limited. In addition, the risk of leakage is substantially reduced. The reason for this is that as the cannula is advanced into the slit septum, a portion of the septum enters into the inner diameter of the cannula and then slides over and around the tip portion of the cannula. By having a smooth interface between the cannula and the slit septum throughout this movement, there is no scoring, slivering or abrasion of the septum surface. As a result, a connector using a smooth cannula may be coupled and uncoupled at least one hundred times without loosing leakage properties. In this respect, a smooth cannula may be defined as a cannula tip which is continuous without a sharp edge through that portion which interfaces the septum. Thus, it has been found that the inside portion of the lumen where the septum touches the wall of the lumen is as important as the geometry of the outside of the cannula in order to maintain a seal and minimize debris. A sharp edge, such as a 90° edge, which is quite common with blunt cannula, especially on the inside portion of the lumen, causes almost instantaneous degradation of leakage properties.

These and other objects and advantages of the invention will become more apparent from the following detailed description taken in conjunction with the accompanying drawings wherein:

FIG. 1 illustrates a cross-sectional view of a prior art blunt cannula;

FIG. 2 illustrates a cross-sectional view of the proximal end of a further known blunt cannula;

FIG. 3 illustrates a cross-sectional view of a smooth cannula constructed in accordance with the invention;

FIG. 4 illustrates a cross-sectional view of another smooth cannula constructed in accordance with the invention;

FIG. 5 illustrates a cross-sectional view of still another smooth cannula constructed in accordance with the invention;

FIG. 6 illustrates a cross-sectional view of the proximal end of a smooth cannula in accordance with the invention mounted in facing relation to a septum in accordance with the invention;

FIG. 7 illustrates a view of the cannula and septum of FIG. 6 during relative movement of the cannula into the septum;

FIG. 7a illustrates an enlarged view of a portion of FIG. 7;

FIG. 8 illustrates an outside view of a valve assembly constructed in accordance with the invention;

FIG. 9 illustrates a view of a modified valve assembly constructed in accordance with the invention;

FIG. 9a illustrates a plan view of a compression ring used in the embodiment of FIG. 9;

FIG. 10 illustrates a further valve assembly constructed in accordance with the invention;

FIG. 10a illustrates a view of the valve assembly of FIG. 10 within a tubular housing in accordance with the invention;

FIG. 11 illustrates a cross-sectional view of female luer connector employing a valve assembly in accordance with the invention;

FIG. 11a illustrates a view of the female luer connector of FIG. 11 connected to a male luer in accordance with the invention;

FIG. 13 illustrates a cross-sectional view of a valve assembly with a wire guide placed therein;

FIG. 13a illustrates a view of the structure of FIG. 13 connected with a male connector for placement of the wire guide;

FIG. 14 illustrates a T-connector employing a valve assembly in accordance with the invention;

FIG. 15 illustrates a view of a Y-site connector employing a valve assembly in accordance with the invention;

FIG. 18 illustrates a series of punches for forming a cannula;

FIG. 19 illustrates a schematic view of a punch for forming an eyelet in the end of a cannula in accordance with the invention;

FIG. 20 illustrates a view of the punch of FIG. 19 impacted against the proximal end of the cannula in accordance with the invention; and FIG. 21 illustrates a cross-sectional view of the proximal end of a cannula formed in accordance with the sequence of steps of FIGS. 18, 19 and 20.

Figure 12:
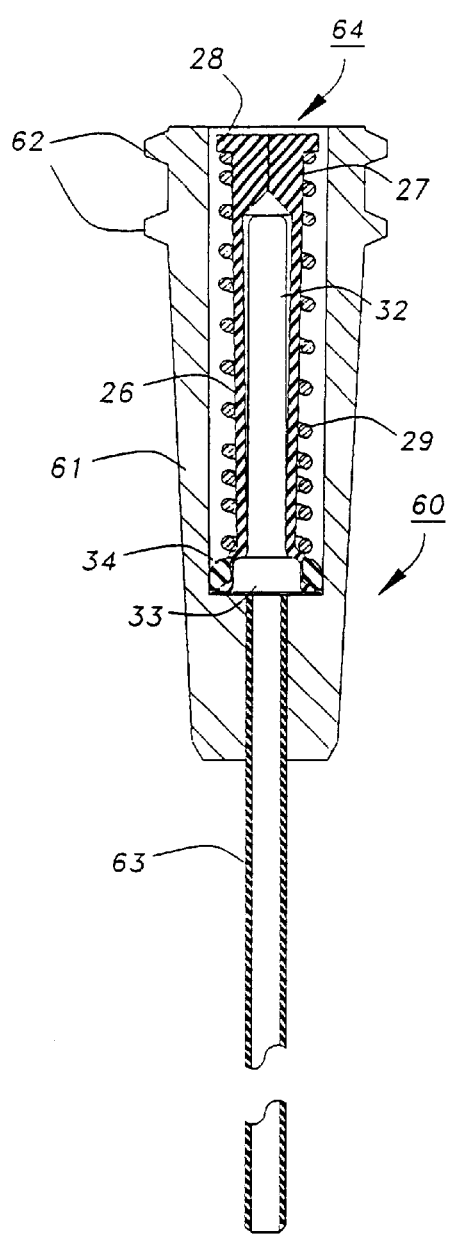
FIG. 12 illustrates a cross-sectional view of a valve assembly in an over-the-needle catheter placement unit in accordance with the invention.

Heretofore, a conventional blunt cannula is typically formed with a proximal end having a flat face such that a sharp corner 11, 12 is formed at the outside diameter and inside diameter of the cannula (FIG. 1) with a rounded corner 14 at the outside diameter but with a sharp corner 15 at the inside diameter.

FIG. 3 illustrates a cross-sectional view of the proximal end of a cannula 16 made in accordance with the invention. In this embodiment, the proximal end of the cannula 16 is rounded such that the proximal end is continuous without a sharp edge.

FIG. 4 illustrates a modified cannula in accordance with the invention wherein the cannula 17 is formed with a proximal end 18 which is folded inwardly of itself to form a rounded tip without a sharp edge.

FIG. 5 illustrates a further modified cannula 19 in accordance with the invention having a proximal end 20 which is folded inwardly of itself while leaving a small gap between the wall of the folded end and the remainder of the cannula 19.

Referring to FIG. 6, a valve connector or assembly 21 constructed in accordance with the invention typically has a hollow smooth cannula 16 disposed within a longitudinally collapsible sleeve 22 across which an elastomeric septum (i.e. membrane) 23 is integrally formed. As indicated, the septum 23 is provided with a passage in the form of a slit 24 or a preformed hole to facilitate passage of the smooth cannula 16 through the septum 23. The cannula 16 has an open proximal end for passage of fluid and this proximal end has a peripheral wall terminating in a smooth surface for penetrating into the septum 23 without removing debris from the septum 23.

During use, as indicated in FIG. 7, the septum 23 is typically moved relative to the cannula 16. In this respect, the proximal end of the cannula 16 abuts against the opposed face of the septum 23. At this time, the central part of the septum 23 moves into the lumen (opening) of the cannula 16. As further indicated in FIG. 7a, the rounded proximal end of the cannula 16 penetrates slightly into the septum 23. Continued relative motion between the cannula 16 and septum 23 causes the surface of the septum 23 to slide along the smooth rounded tip of the cannula 16 without meeting any sharp edge. The material of the septum 23 thus slides over the rounded surface of the cannula tip as the cannula 16 passes through the slit 24 of the septum 23. A means may also be disposed on the septum 27 for circumferentially compressing the septum 27 to close the passage, e.g. the slit 24.

Such a means may be in the form of a coil spring, a split ring, an elastomeric band or a closed ring.

Referring to FIG. 8, a valve assembly 25 constructed in accordance with the invention includes a longitudinally collapsible sleeve 26, for example made of elastomeric material; a septum of elastomeric material 27 integral with the sleeve 26 at one end and having a flange 28 at the distal end; and a coiled spring 29 which abuts the flange 28 on the septum and extends along the length of the sleeve 26. A cannula (not shown) such as described in any one of FIGS. 3, 4 and 5 is disposed within the sleeve 26. As illustrated, the coils of the spring 29 about the septum 27 are of an inner diameter less than the outside diameter of the septum 27 to circumferentially compress the septum 27 in the illustrated extended position of the sleeve 26. This circumferential compression of the septum 27 serves to ensure closure of the slit (not shown) in the septum 27 after repeated passages of a cannula (not shown) therethrough. Of note, as the spring 29 compresses to allow passage of the cannula (not shown) through the septum 27, the coils of the spring expand circumferentially to avoid any interference with passage of the cannula (not shown) through the septum 27.

Referring to FIGS. 9 and 9a, wherein like reference characters indicate like parts as above, a retaining ring 30 may be disposed circumferentially about the septum 27 with an inside diameter less than the outside diameter of the septum 27 to circumferentially compress the septum 27 an amount sufficient to maintain the slit (not shown) of the septum 27 in a closed state upon movement of the septum from a cannula (not shown). As indicated in FIG. 9a, the ring 30 may be split to minimize the force required to penetrate the septum with a smooth cannula.

Alternatively, other means of imposing a compressive force on the septum 27 may be employed, such as the use of a sheath such as a rubberband, or heat-shrink tubing may be used.

Referring to FIG. 10, wherein like reference characters indicate like parts as above, a valve assembly 31 constructed in accordance with the invention may include a cannula 32, as above, formed with a bell-shaped base 33 at a proximal end. In this embodiment, the elastomeric sleeve 26 is stretched over the bell-shaped base 33 and held in place by a retaining ring 34, for example of elastomeric material. As above, a septum 27 is integral with the sleeve 26 and has a flange 28 for abutting the proximal end of a spring 29. The distal end of the spring 29 abuts against the sleeve 26 at the bell-shaped base 33.

Referring to FIG. 10a where like reference characters indicate like parts as above, a valve assembly 35 may be mounted within a tubular housing 36 to form a connector. As indicated, the tubular housing 36 has an internal annular shoulder 37 against which the valve assembly 35 is abutted. In particular, the bell-shaped base 33 of the cannula 32 is used to sandwich the proximal end of the sleeve 26 between the shoulder 37 of the housing 36 and the bell-shaped base 33 of the cannula. Any other suitable of the attachment may also be used.

As illustrated in FIG. 10a, the housing 36 is provided with an external thread 38 to permit securement to another element (not shown). A stop-ring 39 is also provided on the exterior surface of the housing 36 to provide a stop for an element threaded onto the housing 36.

As shown in FIG. 10a, the face of the septum 27 is disposed substantially flush with the end of the housing 36. Thus, the end of the septum 27 can be swabbed. Alternatively, the septum 27 may be recessed within the housing 36 (not shown).

Referring to FIG. 10a, the housing 36 is of the general dimensions of a female luer housing with an inside diameter larger than the septum 27 and sleeve 26. However, the flange 28 of the septum 27 may be larger without generating accessing friction force between the inside wall of the housing 36 and the septum 27 when engaged. The spring 29 is sized to compress the septum 27 about the slit region of the septum 27, which compression may be between 5% and 30% of the outside diameter of the septum 27. It has been found that values lower than 5% result in leakage pressures which, for most uses, are not acceptable. A compression greater than 30% tends to distort the septum 27 and promote excessive abrasion. The spring 29 serves two purposes. First, the spring 29 provides the compression required and secondly gives the septum 27 a snapback or bias when the usual male adaptor coupling (not shown) is removed thereby closing off the connector. Alternatively, the spring need only enclose the septum 27 in order to bias the slit 24 closed since the resiliency of the sleeve 27 can provide a sufficient snapback force.

It has been found that using a cannula 32 with a smooth proximal end, as described above, to convey blood and other fluids to and from a body permit pushing of the septum 27 over the cannula 32 a multiplicity of times. For example, it has been found that the septum 27 may be moved over the cannula 32 one hundred or more times without loss of fluid sealing properties and minimum debris. When a blunt cannula of previously known construction such as shown in FIGS. 1 and 2 or a needle is used, there is almost instantaneous generation of debris. This is objectionable in a clinical situation.

By way of example, the size of elements used for the above tests were as follows:

| | | |
|---|---|---|
| Cannula-OD: | 0.05 inches; ID: | 0.042 inches |
| Length: | 6 inches | |
| Septum - OD: | 0.125 inches at top | |
| Thickness: | 0.022 inches in tubular section | |
| Spring- OD: | 0.133 inches in length with 20 coils per inch. | |

Referring to FIG. 11, a valve connector 40 may be constructed with a hub 41 from which a tubular housing 42 extends in one direction while a female luer connection is formed at the opposite end. As illustrated, a cannula 32 constructed as above is fixedly mounted within the hub 41 and a septum 44 is mounted in the end of the tubular housing 42. In this case, the septum 44 is held in compression by a reduced diameter tubular side wall of the housing 42.

The septum 44 is provided with a shoulder 45 at the proximal end to abut against a shoulder 46 at the distal end of the tubular housing 42. The mating relationship of the shoulders 45, 46 prevents the septum 44 from moving out of the tubular housing 42.

The septum 44 is also provided with a slit 47 in conventional fashion along with an annular skirt 48 which slidably receives the distal end of the cannula 43. A small gap 49 is disposed between the distal end of the cannula 43 and the septum 44. Further, the septum 44 is provided with a recess formed by a conical wall 50 in facing relation to the distal end of the cannula 43. In this respect, the gap 49 which is formed is sized to receive no more than two drops of blood. For example, the gap 49 may have a length of 0.080 inches for a cannula 43 having an O.D. of 0.049 inches.

As further shown in FIG. 11, a coiled spring 51 is disposed concentrically about the cannula 43 concentrically within the tubular housing 42. The spring 51 abuts against the hub 41 of the connector 40 at the proximal end and against the septum 47 at the distal end. In addition, the spring 51 is coiled about the annular skirt 48 of the septum 44. The coils of the spring 51 may circumferentially compress the annular skirt 48 about the distal end of the cannula 43 to provide a sealing effect.

Referring to FIGS. 11a, wherein like reference characters indicate like parts as above, the valve connector of FIG. 11 can be opened, for example using a male luer connector 52. For example, as illustrated, the male luer connector 52 has a tubular portion 53 which is sized to penetrate the tubular housing 42 of the female luer connector 40. In addition, an integral collar 54 is provided on the male luer connector 52 so as to be threadably secured to a thread 38 on the female luer connector 40.

When the tubular portion 53 is penetrated into the tubular housing 42, the septum 44 is pushed inwardly over the cannula 43. At this time, the spring 51 is compressed. The cannula 43 also penetrates into a lumen 55 of the male luer connector 52 so as to permit communication between the lumen 55 of the male luer connector 52, the lumen of the cannula 43 and a lumen 56 of the luer connector 40.

When the male luer connector 52 is removed, the spring 51 biases the septum 44 back into the extended position illustrated in FIG. 11 thereby sealing off the cannula 43.

Referring to FIGS. 11 and 11a, the internal wall of the tubular housing 42 of the connector 40 is of stepped construction so as to have a larger inside diameter proximal of the shoulder 46. This permits the septum 44 to expand when pushed into the tubular portion 42 thereby preventing excessive friction buildup between the septum 44 and the internal wall of the tubular housing 42.

Referring to FIG. 12, wherein like reference characters indicate like parts as above, the valve assembly at FIG. 10 may be mounted in an over-the-needle catheter placement unit 60. As indicated, the unit 60 includes a housing 61 with an external thread 62 at the proximal end. A tube 63 in the form of a plastic cannula extends coaxially from the opposite end of the housing 61 and is secured therein in any suitable fashion. As indicated, the tube 63 is coaxial of the cannula 32 and forms a continuous flow path for a fluid with the cannula 32.

Figure 12A:
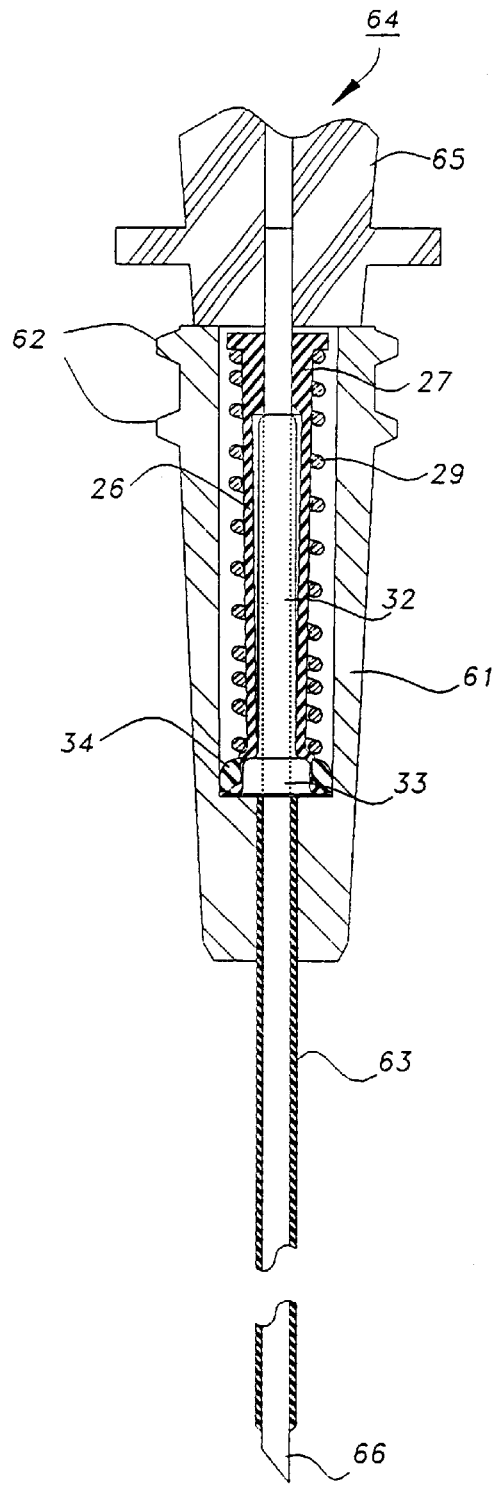
FIG. 12a illustrates a view similar to FIG. 12 with a needle inserted in the placement unit.

The assembly of FIG. 12 may be used to form an IV Over-the-Needle Catheter placement unit, as indicated in FIG. 12a. In this respect, a needle catheter 64 having a hub 65 and needle 66 which extends coaxially from the hub 65 is coupled with the valve assembly of FIG. 12. That is to say, with the septum 27 depressed over the cannula 32 the needle 66 of the catheter 64 is passed through the cannula 32. Thereafter, the septum 27 is through the cannula 32. Thereafter, the septum 27 is allowed to relax into the position shown over the needle 66.

Referring to FIG. 13, wherein like reference characters indicate like parts as above, the unit 60 may be used for placement of a wire guide 68 in a patient. For example, the tube 63 may be in the form of a needle which passes into a vein of a patient (not shown). In addition, as shown in FIG. 13A, a male connector 69 is provided with a central tubular 22 portion 70 for penetrating into the housing 61 to push back the septum 27 over the cannula 32. This exposes the proximal end of the cannula 32 so that the guide wire 68 may be passed into and through the cannula 32 and needle 63 extending from the housing 61 into a patient. Once the wire 68 has been positioned, the male luer connector 69 can be unthreaded from the housing 61 so that the spring 29 biases the septum 27 into the extended condition as shown in FIG. 13. In this condition, the septum 27 seals off the proximal end of the cannula 32 while sealing against the wire 68.

Referring to FIG. 14 wherein like reference characters indicate like parts as above, the valve assembly 31 may be mounted within a tubular portion 71 of a T-connector 72. As indicated, the tubular portion 71 communicates with a transverse conduit 73 of the connector 72.

Referring to FIG. 15, the valve assembly 31 may be mounted within a Y-site connector 74 of conventional structure having a tubular housing adapted to receive the valve assembly 31 in a manner as indicated in FIG. 10a and a side port.

Figure 16:
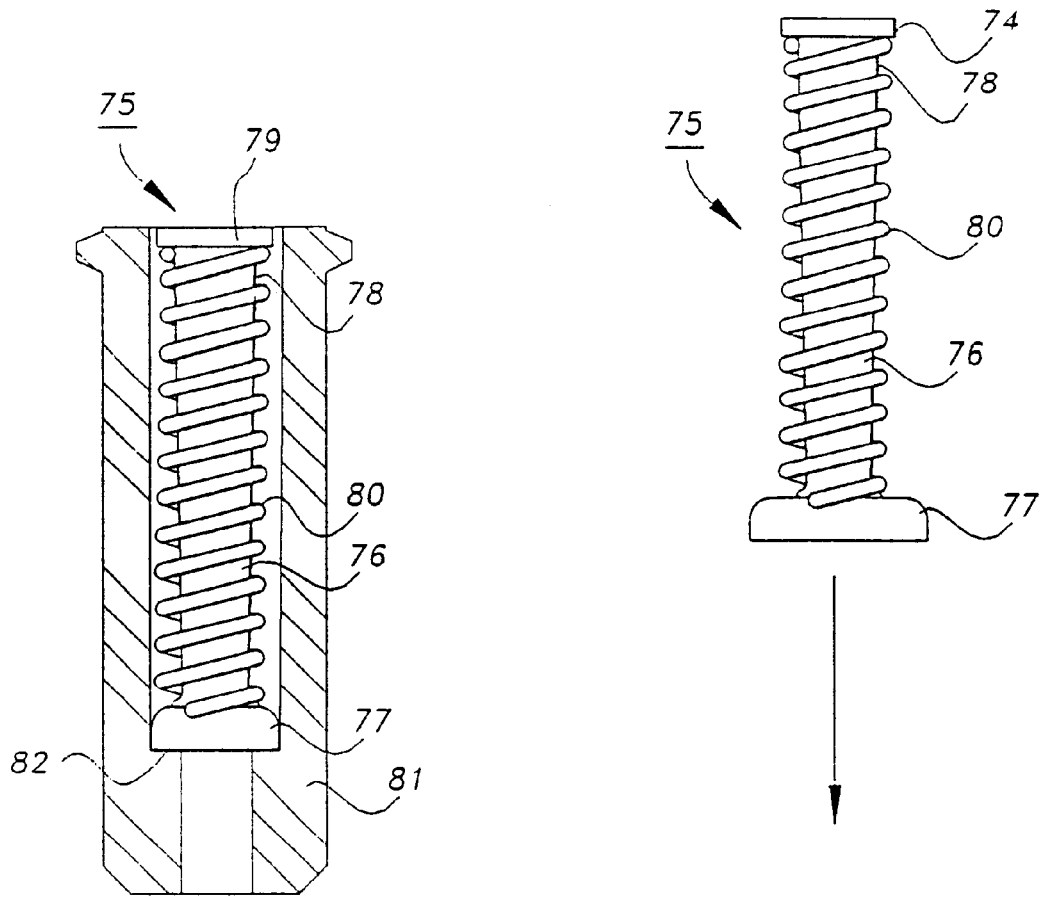
FIG. 16 illustrates a part cross-sectional view of a valve assembly retrofitted in a housing in accordance with the invention.
Figure 17:
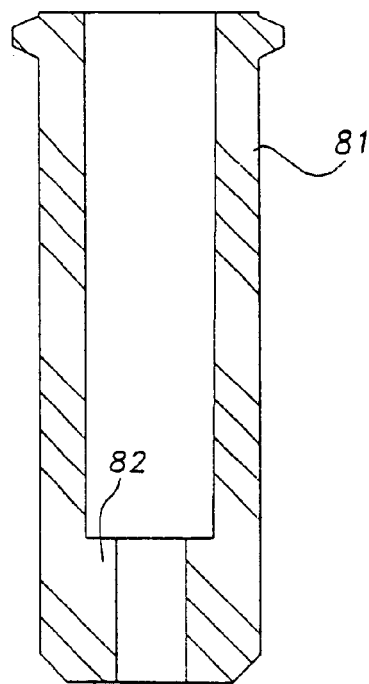
FIG. 17 illustrates an exploded view of the valve assembly and housing of FIG. 16.

Referring to FIGS. 16 and 17, the valve assembly 75 may be constructed with a longitudinally collapsible sleeve 76 having an enlarged flange 77 at the distal end with a septum 78 at the proximal end having an enlarged flange 79 at the distal end. As above, a spring 80 of coil type is disposed concentrically of the sleeve 76 to abut against and between the respective flanges 77, 79 in order to longitudinally expand the sleeve 76. A cannula with a smooth tip (not shown) is disposed within the sleeve 76 in a manner as described above. The unitary valve assembly 75 may be retrofitted into a tubular housing 81 provided with an internal shoulder 82 against which the enlarged flange 77 of the sleeve abuts as indicated in FIG. 16.

Referring to FIGS. 18 to 21, the smooth distal tip of the cannula may be formed using eyelet technology. In this respect, as indicated in FIG. 18, a sheet metal strip 83 is punched by a series of punches 84, 85 . . . ro form into a series of elongated cylinders 86. After reaching an intended length, each cylinder 86 is counter-punched as indicated in FIG. 19 by a punch 87 having a radius or chamfered annular portion 88 at the tip. This punch 87 serves to turn the proximal end of the cylinder 86 inwardly on itself as indicated in FIG. 20 to form a rounded tip 89. As indicated in FIG. 21, the rounded tip 89 may have an inside diameter which is less than the inside diameter of the wall of the cannula 86. However, the sharp inside edge of the rounded tip 89 is substantially recessed within the cannula 86 so as to preclude contact with a septum when in use.

The invention thus provides a blunt cannula having a smooth tip which can be employed in various embodiments to pass through a slit septum without creating any debris. That is to say, the smooth tip of the mouth of the cannula passes over the elastomeric surface of the septum in a sliding manner without exposing any sharp edges to the septum which might otherwise scrape or upbrade the septum.

What is claimed is:
1. The combination of
  a pre-pierced septum of elastomeric material having a passage therein; and
  a hollow needle for penetrating said septum through said passage, said needle having an open promixal end for passage of fluid therethrough, said end having a peripheral wall terminating in a smooth surface at said end for penetrating into said septum, said smooth surface being continuous without a sharp edge.
2. The combination as set forth in claim 1 wherein said peripheral wall is folded inwardly to define said rounded surface.
3. The combination as set forth in claim 1 which further comprises means on said septum for circumferentially compressing said septum to close said passage.
4. In combination,
  a longitudinally collapsible sleeve;
  an elastomeric septum at one end of said sleeve, said septum having a passage therein; and
  a hollow cannula for penetrating said septum through said slit in response to collapsing of said sleeve relative to said cannula, said cannula having an open end for passage of fluid therethrough, said end having a peripheral wall terminating in a smooth surface at said end for penetrating into said septum, said smooth surface being continuous without a sharp edge.
5. The combination as set forth in claim 4 which further comprises a retaining ring disposed circumferentially about said septum, said ring having an inner diameter less than an outer diameter of said septum to circumferentially compress said septum an amount sufficient to maintain said passage in a closed state upon movement of said septum from said cannula.
6. The combination as set forth in claim 5 wherein said ring is split.
7. The combination as set forth in claim 4 which further comprises a coiled spring disposed concentrically of said sleeve and abutting said septum for biasing said sleeve to an extended condition with said septum spaced from said cannula.
8. The combination as set forth in claim 7 wherein said spring has an inside diameter about said septum less than an outside diameter of said septum.
9. The combination as set forth in claim 7 which further comprises a tubular housing having one end of said sleeve mounted therein and being concentrically spaced from said sleeve and said spring to accommodate longitudinal collapsing of said sleeve.
10. The combination as set forth in claim 9 which further comprises a tube mounted in and extending from said housing coaxially of said cannula, said tube communicating with said cannula to convey fluid therebetween.
11. The combination as set forth in claim 10 which further comprises a needle passing coaxially through said septum, said cannula and said tube.
12. The combination as set forth in claim 10 which further comprises a guide wire passing coaxially through said septum, said cannula and said tube.
13. The combination as set forth in claim 12 which further comprises a luer connector removably connected to said housing, said luer connector abutting said septum and collapsing said sleeve relative to said cannula for passage of said guide wire into said open distal end of said cannula.
14. The combination as set forth in claim 9 which further comprises a conduit transverse to and communicating with said tubular housing to define a T-connector.

15. The combination as set forth in claim 9 wherein said tubular housing has a side port communicating therewith to define a Y-site connector.

16. The combination as set forth in claim 4 wherein said sleeve has a flange at an end opposite said septum for abutment of one end of said spring thereon.

17. The combination as set forth in claim 16 which further comprises a tubular housing having said sleeve and said spring disposed concentrically therein, said housing having an internal shoulder receiving said flange of said sleeve thereon.

18. The combination as set forth in claim 4 wherein said septum has a conically shaped recess facing said distal end of said septum.

19. The combination as set forth in claim 4 wherein said distal end of said needle is spaced from said septum to define a gap of 0.080 inches.

20. The combination of
   a tubular housing;
   a hollow cannula concentrically mounted within said tubular housing, said cannula having an open end with a peripheral wall terminating in a smooth surface at said end;
   a septum of elastomeric material having a passage therein mounted at one end of said housing in facing relation to said end of said cannula, and
   a coiled spring concentrically of said cannula and disposed in abutment with said housing and said septum to bias said septum away from said cannula and into circumferential compression with said end of said housing.

21. The combination as set forth in claim 20 wherein said septum has an annular skirt slidably receiving said distal end of said cannula, said skirt being disposed concentrically within said spring.

22. The combination as set forth in claim 21 wherein said septum has a face flush with said end of said housing to allow swabbing thereof.

23. The combination as set forth in claim 20 wherein said housing is a female luer housing.

24. The combination as set forth in claim 20 wherein said housing has an intermediate section extending from said end thereof and being of an inside diameter larger than said outside diameter of said septum.

25. A bloodless IV catheter needle assembly comprising
   a tubular housing;
   a tube extending coaxially from said housing;
   a hollow cannula mounted in said housing coaxially of and in communication with said tube, said cannula having an open end with a peripheral wall terminating in a smooth surface at said end;
   a longitudinally collapsible sleeve disposed about said cannula in seated relation, said sleeve having an elastomeric septum at one end disposed in facing relation to said end of said cannula said septum having a passage therein to permit passage of said cannula through said septum; and
   a coiled spring concentrically of said sleeve and abutting said septum to bias said septum away from said end of said cannula.

26. The combination as set forth in claim 25 wherein said housing has an integral shoulder and said cannula has a bell-shaped base at one end abutting said shoulder.

27. The combination as set forth in claim 26 wherein said sleeve has one end stretched over said base of said cannula end which further comprises a ring circumferentially disposed about said one end of said sleeve and said base to secure said sleeve to said base.

28. The combination as set forth in claim 25 wherein said distal end of said canula is spaced from said septum to define a gap therebetween of 0.080 inches.

29. The combination as set forth in claim 25 wherein said septum has a conically shaped recess facing said distal end of said cannula.

30. The combination of
   A septum of elastomeric material having a slit therein; and
   a hollow cannula for penetrating said septum through said slit and said septum, sand cannula having an open end for passage of fluid therethrough, said end having a peripheral wall terminating in a rounded surface at said end for penetrating into said septum, said rounded surface being continuous without a sharp edge.

31. The combination as set forth in claim 30 wherein said peripheral wall is of uniform thickness.

32. The combination as set forth in claim 30 wherein said peripheral wall is folded inwardly to define said rounded surface.

33. The combination as set forth in claim 30 wherein said cannula has an outside diameter in a range of from 0.032 to 0.058 inches and said septum is of cylindrical shape with an outside diameter in a range of from ¼ to ½ inches.

34. The combination as set forth in claim 30 wherein said peripheral wall is cylindrical.

* * * * *

UNITED STATES PATENT AND TRADEMARK OFFICE
CERTIFICATE OF CORRECTION

PATENT NO. : 6,273,869 B1
DATED : August 14, 2001
INVENTOR(S) : Vincent L. Vaillancourt It is certified that error appears in the above-identified patent and that said Letters Patent is hereby corrected as shown below:

Column 5,
Line 25, change "accessing" to -- excessive --

Column 7,
Line 4, cancel "Thereafter, the septum 27 is through the cannula 32."
Line 49, change "ro" to -- to --

Column 10,
Line 29, change "A" to -- a --.
Line 31, change "sand" to -- said --

Signed and Sealed this

Seventh Day of January, 2003

JAMES E. ROGAN
*Director of the United States Patent and Trademark Office*